United States Patent
Lang et al.

(10) Patent No.: US 10,226,044 B2
(45) Date of Patent: Mar. 12, 2019

(54) AGRICULTURAL AND HORTICULTURAL COMPOSITION AND METHOD FOR CULTIVATING PLANT

(71) Applicant: AJINOMOTO CO., INC., Tokyo (JP)

(72) Inventors: Yaqin Lang, Kanagawa (JP); Yang Chen, Kanagawa (JP); Satoru Kondo, Chiba (JP); Shunji Suzuki, Yamanashi (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/247,254

(22) Filed: Aug. 25, 2016

(65) Prior Publication Data

US 2017/0000122 A1    Jan. 5, 2017

Related U.S. Application Data

(63) Continuation of application No. PCT/JP2015/055740, filed on Feb. 27, 2015.

(30) Foreign Application Priority Data

Feb. 28, 2014 (JP) .................................. 2014-038981

(51) Int. Cl.
*A01G 7/06* (2006.01)
*A01G 22/05* (2018.01)
(Continued)

(52) U.S. Cl.
CPC ............... *A01N 37/44* (2013.01); *A01G 7/06* (2013.01); *A01G 22/00* (2018.02); *A01G 22/05* (2018.02);
(Continued)

(58) Field of Classification Search
CPC . A01G 1/00; A01G 1/001; A01G 7/06; A01G 22/05; A01G 22/20
(Continued)

(56) References Cited

U.S. PATENT DOCUMENTS 4,964,894 A * 10/1990 Freepons ............... A01N 43/16
                                                                 47/57.6
5,318,788 A    6/1994 Yokota et al.
(Continued)

FOREIGN PATENT DOCUMENTS

CN    102285823 A    12/2011
CN    101891520 B    8/2012
(Continued)

OTHER PUBLICATIONS

International Preliminary Report on Patentability for PCT Patent App. No. PCT/JP2015/055740 (dated Sep. 15, 2016).
(Continued)

*Primary Examiner* — David J Parsley
(74) *Attorney, Agent, or Firm* — Cermak Nakajima & McGowan LLP; Shelly Guest Cermak

(57) ABSTRACT

A composition for agricultural or horticultural application, which contains isoleucine as an active ingredient, and is sprinkled on a fruit vegetable, fruit tree, or grain plant, or a harvested fruit as a solution having an isoleucine concentration of 0.5 to 75 mM, is sprinkled on a leaf surface and/or a fruit of a plant to provide at least one of promotion of blooming, promotion of the appearance of the fruit, improvement in number of fruit produced, promotion of ripening of fruit, improvement in essential amino acid and/or γ-ABA content, promotion of carotenoid synthesis, and improvement in antioxidant capacity.

10 Claims, 11 Drawing Sheets
(4 of 11 Drawing Sheet(s) Filed in Color)
Specification includes a Sequence Listing.

(51) Int. Cl.
*A01G 22/20* (2018.01)
*A01N 37/44* (2006.01)
*C05F 11/10* (2006.01)
*C05F 11/00* (2006.01)
*A01G 22/00* (2018.01)

(52) U.S. Cl.
CPC .............. *A01G 22/20* (2018.02); *C05F 11/00* (2013.01); *C05F 11/10* (2013.01)

(58) Field of Classification Search
USPC .......................... 47/58.1 FV, 58.1 R, 58.1 SE
See application file for complete search history.

(56) References Cited

U.S. PATENT DOCUMENTS

| | | | | |
|---|---|---|---|---|
| 6,471,741 | B1* | 10/2002 | Reinbergen | A01N 63/00 435/243 |
| 2013/0190173 | A1* | 7/2013 | Panicheva | C05G 3/02 504/101 |
| 2013/0303377 | A1 | 11/2013 | Quaghebeur | |

FOREIGN PATENT DOCUMENTS

| | | |
|---|---|---|
| CN | 102627498 A | 8/2012 |
| JP | 49-91829 S | 9/1974 |
| JP | 2003-48803 A | 2/2003 |
| JP | 2007-259714 A | 10/2007 |
| JP | 2009-240171 A | 10/2009 |
| JP | 2012-10694 A | 1/2012 |
| JP | 2012-197249 A | 10/2012 |
| JP | 2013-43800 A | 3/2013 |
| KR | 10-2013-0095524 A | 8/2013 |
| KR | 10-2013-0107406 A | 10/2013 |

OTHER PUBLICATIONS

Concha, C. M., et al., "Methyl jasmonate treatment induces changes in fruit ripening by modifying the expression of several ripening genes in *Fragaria chiloensis* fruit," Plant Phys. Biochem. 2013;70:433-444.

Fonseca, S., et al., "The jasmonate pathway: the ligand, the receptor and the core signalling module," Curr. Op. Plant Biol. 2009;12:539-547.

Fonseca, S., et al., "(+)-7-iso-Jasmonoyl-L-isoleucine is the endogenous bioactive jasmonate," Nature Chem. Biol. 2009;5(5):344-350.

International Search Report for PCT Patent App. No. PCT/JP2015/055740 (Mar. 31, 2015).

Kramell, R., et al., "Occurrence and Identification of Jasmonic Acid and Its Amino Acid Conjugates Induced by Osmotic Stress in Barley Leaf Tissue," J. Plant Growth Regul. 1995;14:29-36.

Krumm, T., et al., "Induction of volatile biosynthesis in the Lima bean (*Phaseolus lunatus*) by leucine- and isoleucine conjugates of 1-oxo- and 1-hydroxyindan-4-carboxylic acid: evidence for amino acid conjugates of jasmonic acid as Intermediates in the octadecanoid signalling pathway," FEBS Lett. 1995;377:523-529.

Liu, L., et al., "Ethylene independent induction of lycopene biosynthesis in tomato fruits by jasmonates," J. Experimen. Botany 2012;63(16):5751-5761.

Nun, N. B., et al., "Possible function of isoleucine in the methyl jasmonate response of *Arabidopsis* to *Phelipanche aegyptiaca*," Phytoparasitica 2009;37:485-488.

Pang, S.-T., et al., "Effects of different foliar fertilizers on the physiology and biochemistry of tomato and population ecology of *Bemisia tabaci*," Chinese J. Eco-Agriculture 2013;21(4):465-473, with English translation thereof.

Qu, J.-G., et al., "Significant Improved Anthocyanins Biosynthesis in Suspension Cultures of *Vitis vinifera* by Process Intensification," Chinese J. Biotechnol. 2006;22(2):299-305, with English translation thereof.

Wang, L.-J., et al., "Promotion of L-Glutamic acid on anthocyanin accumulation of Fuji apples," J. Fruit Sci. 2006;23 (2):157-160, with English language translation thereof.

Wang, H.-J., et al., "Effects of Amino Acids Replacing Nitrate on Growth, Nitrate Accumulation, and Macroelement Concentrations in Pak-choi (*Brassica chinensis* L.)," Pedosphere 2007;17(5):595-600.

Wasternack, C., et al., "Jasmonates: biosynthesis, perception, signal transduction and action in plant stress response, growth and development. An update to the 2007 review in Annals of Botany," Annals of Botany 2013;111:1021-1058.

Wu, X.-P., et al., "Effects of Extraneous Source Amino Acid on the Contents of Amino Acid of Tobacco Leaves," Scientia Agricultura Sinica 2004;37(3)357-361, with English language translation thereof.

Pérez, A. G., et al., "Biosynthesis of Strawberry Aroma Compounds through Amino Acid Metabolism," J. Agric. Food Chem. 2002;50:4037-4042.

Wilchem: "Flower 'n' Fruit Maker" Brochure, May 15, 2013, pp. 1-4, XP055394344, Retrieved from the Internet on Jul. 27, 2017, http://www.wilchem.com.au/uploads/Brochures/Flower N Fruit Maker Brochure.pdf.

Extended European Search Report for European Patent App. No. 15755538.4 (dated Aug. 7, 2017).

* cited by examiner

AGRICULTURAL AND HORTICULTURAL COMPOSITION AND METHOD FOR CULTIVATING PLANT

This application is a Continuation of, and claims priority under 35 U.S.C. § 120 to, International Application No. PCT/JP2015/055740, filed Feb. 27, 2015, and claims priority therethrough under 35 U.S.C. § 119 to Japanese Patent Application No. 2014-038981, filed Feb. 28, 2014, the entireties of which are incorporated by reference herein. Also, the Sequence Listing filed electronically herewith is hereby incorporated by reference (File name: 2016-08-25T_US-548_Seq_List; File size: 4 KB; Date recorded: Aug. 25, 2016).

BACKGROUND OF THE INVENTION

Field of the Invention

The present invention relates to a composition for agricultural or horticultural application, and a method for cultivating a plant. More precisely, the present invention relates to a composition for agricultural or horticultural application that can promote blooming and the appearance of fruit of a plant, the ripening and/or change in color of fruit before and after harvest, and so forth, and uses thereof.

Brief Description of the Related Art

In order to improve the growth of crops and the quality of fruits harvested or nuts harvested from those crops, chemical fertilizers, phytohormones, and so forth are used. However, these methods have unsolved problems concerning their influence on the environment and their cost. Amino acids are known to be environmentally friendly and inexpensive ingredients of compositions for agricultural or horticultural application. For example, a flower bud formation-promoting agent using proline as an active ingredient (Japanese Patent Laid-open (Kokai) No. 2003-48803), a plant high temperature stress resistance-imparting agent containing a branched chain amino acid such as valine or leucine (Japanese Patent Laid-open (Kokai) No. 2012-197249), a plant growth-promoting liquid fertilizer containing 18 kinds of amino acids (South Korean Patent Laid-open No. 2013-107406), a plant allelopathy effect and/or phytoalexin production-enhancing agent containing an amino acid fermentation by-product or a nucleic acid fermentation by-product (Japanese Patent Laid-open (Kokai) No. 2012-10694), and so forth, have been reported. Hydroponics of tobacco in an aqueous solution containing glutamic acid, aspartic acid, and phenylalanine have been reported to increase the content of amino acids, chlorophylls, and carotenoids in the leaves (Wu, X-P. et al., Scientia Agricultura Sinica, 2004, 37(3):357-361).

The aforementioned plant growth-promoting liquid fertilizer (South Korean Patent Laid-open No. 2013-107406) contains 0.05% of isoleucine, and the concentration thereof in a liquid to be sprinkled is 0.019 to 0.076 mM. Furthermore, Japanese Patent Laid-open (Kokai) No. 2012-10694 describes that a treatment of rice seeds with 0.2 to 20 mM isoleucine promoted production of momilactones A and B.

It is known that jasmonic acid, which is a kind of phytohormone, has physiological actions including those for topogenesis, such as the formation of flower and formation of tuber, and transcription-activating actions for genes that respond to stresses such as insect damages and diseases (New Science of Phytohormones). It has also been reported that a treatment of fruits or berries such as tomatoes and strawberries with methyl jasmonate promotes the appearance of fruit or the ripening or change in color (Liu, L., Journal of Experimental Botany, 2012, 63(16):5751-5761 and Concha, C. M. et al., Plant Physiology and Biochemistry, 2013, 70:433-444).

It is known that, in the jasmonic acid signal transduction, (+)-7-iso-JA-Ile consisting of jasmonic acid and isoleucine bound together constitutes the active type (Fonseca, S. et al., Plant Biology, 2009, 12:539-547, Fonseca, S. et al., Nature Chemical Biogogy, 2009, 5:344:350, and Wasternack, C., Annals of Botany, 2013, 111:1021-1058).

As for the relation of isoleucine and jasmonic acid, it was reported that infection of *Phelipanche aegyptiaca*, which is a plant parasite, in *Arabidopsis thaliana* cultivated on an agar medium was suppressed by a treatment of the plant with a mixture of isoleucine and methyl jasmonate, whereas a treatment with isoleucine alone was ineffective (Nun, N. B. et al., Phytoparasitica, 2009, 37(5):485-488). It has also been demonstrated that treating lima bean seedlings with immersion in a solution of a complex of leucine or isoleucine, and 1-oxoindane-4-carboxylic acid or 1-hydroxyindane-4-carboxylic acid, induces synthesis of volatile substances involved in insect resistance, and a complex of an amino acid and jasmonic acid is an intermediate of the octadecanoid signal transduction pathway (Krumm, T. et al., FEBS Letters, 1995, 377(3):523-529).

It was also reported that by treating barley leaves with immersion in a solution for inducing osmotic pressure stress (D-sorbitol, D-mannitol, polyethylene glycol 6000, and sodium chloride) increased jasmonic acid and complex of jasmonic acid and an amino acid (Kramell, R. et al., Journal of Plant Growth Regulation, 1995, 14(1):29-36).

There has also been a report concerning the influences of branched chain amino acids and so forth on growth and nutritional state of tomatoes, as well as growth, survival, and proliferation of *Bemisia tabaci* (Pang, S-T. et al., Chinese Journal of Eco-Agriculture, April 2013, 21(4):465-473). The concentration of isoleucine used for the treatment described in this report is 0.012 to 0.035 mM.

It has also been reported that mixed fertilizers containing various amino acids, trace ingredients, and phytohormones increase fruit ratio and crop yield of plant fruits (Chinese Patent Laid-open No. 102627498). The concentration of isoleucine used for the treatment described in this report is 1.1 to 4.3 nM.

It has also been reported that foliar spray fertilizers containing various amino acids, trace ingredients, xanthine, etc. have plant fruit-increasing effects, saccharide content-increasing effects, and so forth (Chinese Patent Laid-open No. 102285823), and that foliar spray fertilizers containing trace ingredients and various amino acids increase crop yield of Chinese cabbage (Chinese Patent No. 101891520). It has further been reported that glutamic acid increases anthocyanin of apple (Wang, L. J., Journal of Fruit Science, 2006, 23(2):157-160), and that phenylalanine increases anthocyanin of grape (Qu, J. G. et al., Sheng Wu Gong Cheng Xue Bao, 2006, 22(2):299-305). It has also been reported that methionine promotes ripening of fruits (Japanese Patent Laid-open (Kokai) No. 2007-259714).

As described above, there have been reported several findings concerning the effects of isoleucine and other amino acids on plants, but it is not known that application of a high concentration isoleucine solution by sprinkling promotes blooming and the appearance of fruit of plants, ripening of harvested fruits, and so forth.

In addition, it was reported that, when examining the influences of substitution of each of 20 kinds of amino acids for 20% of nitrate nitrogen in a nutrient solution on growth of bok choy in hydroponics, isoleucine increased nitrogen and phosphorus contents of terrestrial parts (shoots) of the plant, but it was not effective on the growth (weight of root clump) (Wang, H-J. et al., Pedosphere, 2007, 17(5):595-600).

SUMMARY OF THE INVENTION

An aspect of the present invention is to provide a safe composition for agricultural or horticultural application that can promote blooming and the appearance of fruits of a plant, the ripening or change in color of fruits, an increase of the essential amino acid and/or γ-aminobutyric acid (γ-ABA) content, or ripening or change in color of harvested fruit, and improves crop yield of high quality plant crop (fruit or grain) in a short period of time.

It has been found and is described herein that, for example, sprinkling of an isoleucine solution on a plant promoted blooming and the appearance of fruit, as well as the ripening of fruit of the plant. Furthermore, it was found that the sprinkling of an isoleucine solution on fruit promoted a change in color or ripening of the fruit, and that sprinkling of an isoleucine solution eventually enabled production of high quality plant crops with improved crop yield in a short period of time.

The present invention thus provides the following:

It is an aspect of the present invention to provide a method for cultivating a plant, which comprises sprinkling a solution comprising 0.5 to 75 mM of isoleucine on a fruit vegetable, a fruit tree, or a grain plant.

It is a further aspect of the present invention to provide the method as described above, wherein isoleucine is L-isoleucine.

It is a further aspect of the present invention to provide the method as described above, wherein isoleucine is selected from the group consisting of purified isoleucine, a fermentation liquid or a fermentation by-product of isoleucine, and a fractionation product of a fermentation liquid or a fermentation by-product of isoleucine.

It is a further aspect of the present invention to provide the method as described above, wherein the sprinkling of the solution provides an effect selected from the group consisting of: a) promotion of blooming, b) promotion of the appearance of the fruit, c) improvement in number of fruit produced, d) promotion of ripening of fruit, e) improvement in essential amino acid and/or γ-aminobutyric acid content, f) promotion of carotenoid synthesis, g) improvement in antioxidant capacity, and h) combinations thereof.

It is a further aspect of the present invention to provide the method as described above, wherein the solution is sprinkled on a fruit vegetable or a fruit tree.

It is a further aspect of the present invention to provide the method as described above, wherein the plant belongs to the family Solanaceae, Vitaceae, or Rosaceae.

It is a further aspect of the present invention to provide the method as described above, wherein the plant is able to produce a fruit selected from the group consisting of tomato, pepper, grape, and apple.

It is a further aspect of the present invention to provide the method as described above, wherein the solution is sprinkled on a leaf surface and/or a fruit.

It is an aspect of the present invention to provide a method for promoting ripening after harvest of a fruit, which comprises sprinkling a solution containing 0.5 to 75 mM of isoleucine on a harvested fruit.

It is a further aspect of the present invention to provide the method for promoting ripening after harvest as described above, wherein the isoleucine is L-isoleucine.

It is a further aspect of the present invention to provide the method for promoting ripening after harvest as described above, wherein the isoleucine is selected from the group consisting of purified isoleucine, a fermentation liquid or a fermentation by-product of isoleucine, and a fractionation product of a fermentation liquid or a fermentation by-product of isoleucine.

It is a further aspect of the present invention to provide the method for promoting ripening after harvest as described above, wherein the sprinkling of the solution provides an effect selected from the group consisting of: a) promotion of ripening of the fruit, b) improvement in essential amino acid and/or γ-aminobutyric acid content of the fruit, c) promotion of carotenoid synthesis of the fruit, d) improvement in antioxidant capacity of the fruit, and e) combinations thereof.

It is a further aspect of the present invention to provide the method for promoting ripening after harvest as described above, wherein the fruit is a fruit of a plant belonging to the family Solanaceae, Vitaceae, or Rosaceae.

It is a further aspect of the present invention to provide the method for promoting ripening after harvest as described above, wherein the fruit is selected from the group consisting of tomato, grape, and apple.

It is also an aspect of the present invention to provide a composition for agricultural or horticultural application, which comprises isoleucine as an active ingredient in a concentration of 0.5 to 75 mM.

BRIEF DESCRIPTION OF THE DRAWINGS

The patent or application file contains at least one drawing executed in color. Copies of this patent or patent application publication with color drawings will be provided to the Office upon request and payment of the necessary fee.

FIG. 5a shows number of colored fruit, in which the vertical axis indicates number of colored fruit per four root clumps, and FIG. 5b includes photographs of fruit produced by blooming on the same day (appearance of fruit).

DESCRIPTION OF THE PREFERRED EMBODIMENTS

Figure 1:
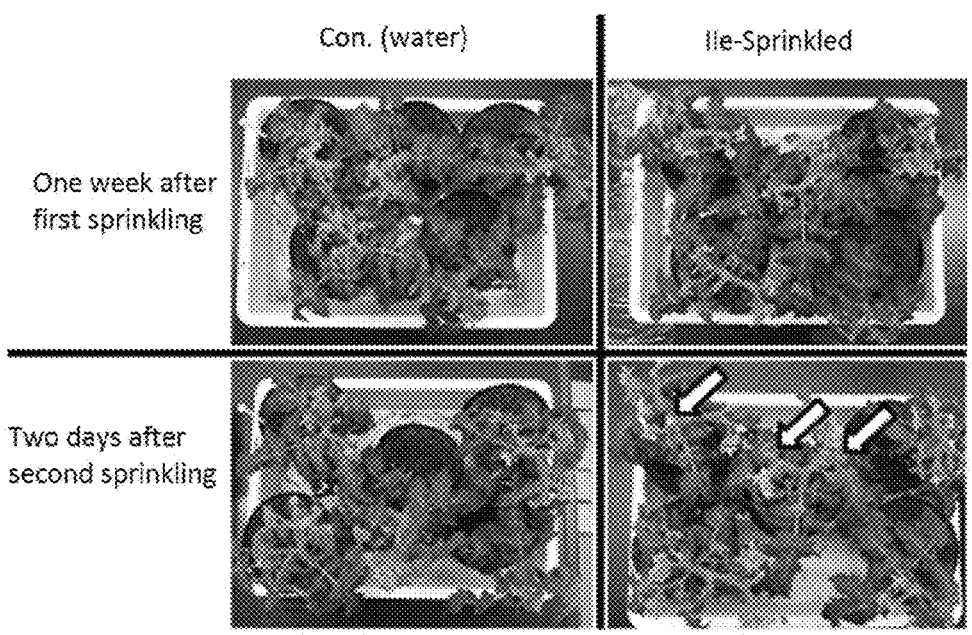
FIG. 1 includes photographs showing the blooming and appearance of tomatoes sprinkled with isoleucine (photographs showing morphologies of the plants). The arrows point at the fruit.

Hereafter, the present invention will be explained in detail.

The composition for agricultural or horticultural application contains isoleucine as an active ingredient. Isoleucine can be L-isoleucine. The amino acids can be referred to as L-amino acids, unless otherwise noted. Isoleucine can be purified isoleucine or roughly purified isoleucine, or isoleucine can be within a culture (fermentation liquid) or fermentation by-product, or a fractionation product of any of a culture or fermentation by-product.

The composition for agricultural or horticultural application can contain one or more other arbitrary ingredients in addition to isoleucine, so long as the effect of the composition is not degraded. Examples of such ingredients can include a carrier, pH adjustor, fertilizer component for enhancing fertilizing effect such as minerals, agrochemical ingredient, binder, filler, and so forth. As these ingredients, ingredients usually used for agricultural chemicals, fertilizers, and so forth can be used, so long as the effect of the composition is not degraded.

The composition for agricultural or horticultural application can also contain one or more amino acids other than isoleucine.

The dosage form of the composition for agricultural or horticultural application is not particularly limited so long as a solution that can be sprinkled can be prepared from it at the time of use, and it can be provided in the form, such as a solution, powder, granule, emulsion, and so forth.

When the composition for agricultural or horticultural application is sprinkled on a plant, it can be sprinkled on a leaf surface and/or a fruit as described herein. A spreading agent can be added in order to enhance spreading power of the composition for agricultural or horticultural application on a leaf surface or fruit, and such an ingredient as surfactant can be added in order to enhance permeability of isoleucine into the plant. Examples of the spreading agent include, for example, Applauch BI™ (Kao), Mix Power™ (Syngenta Japan), Squash™ (MARUWA Biochemical), and so forth. As the surfactant, any of nonionic surfactants, anionic surfactants, cationic surfactants, and ampholytic surfactants can be used. Examples include polyoxyethylene alkyl ethers, polyoxyethylene alkyl aryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphoric acid esters, fatty acid salts, alkylsulfuric acid ester salts, alkylsulfonic acid salts, alkylarylsulfonic acid salts, alkylphosphoric acid salts, alkylphosphoric acid ester salts, polyoxyethylene alkylsulfuric acid esters, quaternary ammonium salts, oxyalkylamines, lecithin, saponin, and so forth. In addition, gelatin, casein, starch, agar, polyvinyl alcohol, sodium alginate, and so forth can be used as an auxiliary agent as required.

At the time of use of the composition for agricultural or horticultural application, the composition in the form of solid or powder can be dissolved or dispersed in a solvent such as water and alcohol. The composition for agricultural or horticultural application in the form of liquid can be diluted with a solvent such as water and alcohol at the time of use thereof. Examples of the alcohol include ethanol, methanol, isopropyl alcohol, and so forth.

Isoleucine content in the composition for agricultural or horticultural application is not particularly limited so long as the composition can be sprinkled on a plant or harvested fruit at the prescribed isoleucine concentration described below at the time of applying the composition. The composition for agricultural or horticultural application can be in the form of solid or solution. However, when it is a solution, the isoleucine concentration can be, for example, 0.5 mM to the saturated concentration. The solubility of isoleucine in water is about 0.3 M (40.2 g/L (20° C.), 41.2 g/L (50° C.)).

The isoleucine concentration at the time of application of the composition for agricultural or horticultural application can be 0.5 to 75 mM, 0.5 to 50.0 mM, 1.0 to 20.0 mM, or 5.0 to 10.0 mM. Although the isoleucine content in the composition for agricultural or horticultural application is not particularly limited, it can be 1% by weight or higher, 50% or higher, 70% or higher, in terms of dry weight, and an isoleucine content within the range exemplified above is on example in view of avoiding damage from impurities such as salt injury, and actualization of effect of isoleucine.

The composition for agricultural or horticultural application has at least one of the following effects: blooming-promoting action, appearance of fruit-promoting action, fruit number produced-improving action, fruit ripening-promoting action, essential amino acid and/or γ-aminobutyric acid content-improving action, carotenoid synthesis-promoting action, and antioxidant capacity-improving action. Therefore, the composition for agricultural or horticultural application can be used for promotion of blooming, promotion of appearance of fruit, improvement in number of fruit produced, promotion of ripening of fruits, improvement in essential amino acid and/or γ-aminobutyric acid content, promotion of carotenoid synthesis, and improvement in antioxidant capacity, and can, as a result, improve crop yield of a plant and/or quality of crops in a short period of time.

The object of the application of the agricultural or horticultural composition is not particularly limited so long as any of the aforementioned actions occurs. The object to which the agriculture or horticultural composition can be applied can include a "fruit vegetable" (vegetables, the fruits of which are used as foods), fruit trees, grain plants, and so forth, before blooming. The object can be a fruit of the fruit vegetable plant, fruit tree, or grain plant after blooming.

Examples of a fruit vegetable include tomato (including cherry tomato), okra, eggplant, pepper, cucumber, melon, bitter cucumber, Japanese pumpkin, oriental melon, chayote, watermelon, strawberry, soybean, adzuki bean, broad bean, pea, peanut, cowpea, lupin, clover, alfalfa, and so forth.

Examples of a fruit tree include such fruit trees as Chinese quince, Chinese white pear, pear, quince, common medlar, Juneberry, shipova, apple, American cherry, apricot, plum, cherry, sour cherry, blackthorn, Japanese plum, peach, almond, ginkgo tree, chestnut, walnut, pecan, akebi, fig, Japanese persimmon, bramble, kiwi fruit, oleaster, mulberry, cranberry, mountain cranberry, pomegranate, tara vine, seabuckthorn, currant, jujube, Japanese bush cherry, bilberry, redcurrant, grape, blackberry, blueberry, pawpaw, *Schisandra nigra*, raspberry, downy cherry, those of genus *Citrus*, *Fortunella* or *Poncirus*, olive, loquat, bayberry, and so forth.

A grain plant is a plant, the seeds of which are used as foods, and examples thereof include wheat, barley, rice, corn, sorghum, millet, oat, rye, triticale, buckwheat, and so forth.

Varieties of the fruit vegetable are not particularly limited, and examples for tomato (including cherry tomato) include, for example, Momotaro, Roma, Ouju, First Tomato, Akairomarutama, Yellow Carol, Paruche, Mini Carol, Micro-Tom, Suncherry Pure, and so forth.

Examples of pepper varieties include Anaheim, bell pepper, green pepper, chili pepper (Takanotusme), Manganji green pepper, paprika, habanero, jolokir, jalapeno, and so forth.

Varieties of the fruit tree are not particularly limited, and examples for grape include, for example, Cabernet Sauvignon, Chardonnay, Tempranillo, Pinot Noir, muscat, Koshu, Kaiji, Kyoho, Pione, and so forth.

Examples for apple include Tsugaru, Fuji, Golden Delicious, Kougyku, Kokko, Mutsu, Ohrin, Johnna Gold, and so forth.

Exemplary plants are plants that bear fruit, including both fruit vegetables and fruit trees. Particular examples are plants belonging to the family Solanaceae, Vitaceae, or Rosaceae, and tomato, pepper, grape, and apple.

The method of the present invention is a method for cultivating a plant, which includes sprinkling a solution containing 0.5 to 75 mM of isoleucine to a fruit vegetable, fruit tree, or grain plant. Another aspect of the present invention is a method for cultivating a plant, which includes sprinkling the agricultural or horticultural composition to a plant leaf surface and/or the fruit to improve and/or promote at least one of blooming, ability to bear fruit, the number of fruit produced, the ripening of the fruit, essential amino acid and/or γ-aminobutyric acid content, carotenoid synthesis, and/or antioxidant capacity.

The solution containing 0.5 to 75 mM of isoleucine can be prepared by dissolving the composition for agricultural or horticultural application in a solvent, and diluting the resulting solution as required.

As the plant body to which the agricultural or horticultural composition is sprinkled, a leaf or fruit can be used. Foliar application is a particular example. The foliar application means that the composition can be sprinkled to at least a leaf surface, and the composition can be sprinkled to other parts in addition to a leaf surface. The same shall apply to fruit.

The composition for agricultural or horticultural application can be sprinkled on a harvested fruit. By sprinkling the composition for agricultural or horticultural application on a fruit, ripening after harvest can be promoted. Promotion of ripening after harvest can include promotion of coloring, increasing lycopene content, increasing sugar content, and increasing amino acid content such as glutamic acid content.

Another aspect of the present invention is a method for promoting or improving at least one of blooming, appearance of fruit, number of fruit produced, ripening of fruit, essential amino acid and/or γ-ABA content, carotenoid synthesis, and/or antioxidant capacity, which can include applying the agricultural or horticultural composition to a plant. This method is a method for cultivating a plant, which improves crop yield of a plant, improves quality of crops, promotes growth in a short period of time, or permits earlier harvest.

Another aspect of the present invention is a method for promoting ripening after harvest of a fruit, which can include applying the agricultural or horticultural composition to a harvested fruit.

Examples of amino acids, the content of which can be improved, include essential amino acids. Such essential amino acids can include at least one of tryptophan, lysine, threonine, valine, leucine, isoleucine, and histidine.

Although the amount of the agricultural or horticultural composition to be sprinkled is not particularly limited, it can be 6.5 to 3000 g/ha, 6.5 to 2000 g/ha, 13 to 800 g/ha, or 65 to 400 g/ha, in terms of amount of isoleucine.

When the composition is applied to a harvested fruit, the amount can be 0.002 to 0.3 g/g (fruit), 0.002 to 0.2 g/g (fruit), 0.004 to 0.08 g/g (fruit), or 0.02 to 0.04 g/g (fruit), in terms of amount of isoleucine.

The time of applying the agricultural or horticultural composition to a plant can be appropriately determined depending on the desired effect. For example, it can be applied before blooming if the promotion of blooming is desired, before the appearance of fruit or after the appearance of fruit if the promotion of appearance of fruit or improvement in the number of fruit produced is desired, or after the appearance of fruit and before harvest if the promotion of ripening (turning color) is desired. The number of times of application is not particularly limited, and it can be applied once, or two or more times.

Although the sprinkling method for sprinkling the composition for agricultural or horticultural application is not particularly limited, the agricultural or horticultural composition can be be sprinkled so that the composition spreads over the entire terrestrial part of the plant, including the foliage and fruit, including the leaf surfaces and/or fruit. When the composition is manually sprinkled, it can be sprinkled with a spray nozzle which directs the composition onto the leaf surface or the underside of the leaf. When a boom sprayer is used, the volume of the solution to be sprinkled can be 100 L or larger, 200 to 3000 L, or 300 to 2000 L, per 1 ha. The so-called electrostatic sprayer or electrostatic spraying nozzle that promotes adhesion of the sprayed solution to plant bodies using static electricity can also be used.

When the agricultural or horticultural composition is sprinkled on leaf surfaces and/or fruit, the composition can be mixed with a fertilizer for foliar application usually used in agriculture.

When a plant is cultivated according to the method of the present invention, amounts and application methods of basal fertilizer and additional fertilizer to be applied to the soil can be similar to those used in that part of the region according to the type of the plant to be cultivated. When a plant is cultivated according to the method of the present invention, cultivation density can be a density recommended in that part of the region according to the type of the plant to be cultivated. However, when the composition is sprinkled on leaf surfaces and/or fruit, furrow (interrow space) can be 20 cm or wider so that the sprayed materials can also easily reach lower leaves.

EXAMPLES

Hereafter, the present invention will be more specifically explained with reference to the following non-limiting examples.

Example 1: Effect of Isoleucine on Cherry Tomato (Micro-Tom)

Three seeds of cherry tomato (Micro-Tom) were shown in compost contained in a slit pot (upper diameter 10.5 cm×height 8.8 cm), and cultivated in a biotron at a temperature of 23° C. with a light period of 14 hours (6:00 to 20:00) and dark period of 10 hours (20:00 to 6:00). As the compost, a mixture of Kumiai Nippi Engei Baido No. 1 (Nihon Hiryo) and vermiculite at a ratio of 3:1 (volume ratio) was used.

After 3 weeks, one root clump was left, and the others were thinned out. From one month after the sowing to harvest, a 300-fold diluted solution of Hyponex liquid fertilizer (N:P:K=6:10:5, Hyponex Japan) was additionally applied as soil fertilizer by irrigation at a frequency of once a week in a volume of 100 mL per one root clump (pot).

After the plants of five root clumps uniformly grew, and flower buds began to appear, water (Control, or Con) or 10 mM L-isoleucine aqueous solution (Ile) was sprinkled on the whole plants once a week. The sprinkled volume was 5 mL per one root clump.

Then, the blooming, appearance of fruit, ripening of the fruit, and number of fruit produced were investigated for each root clump.

i) Blooming and Appearance of Fruit

The blooming states of the plants are shown in FIG. 1. Blooming and appearance of the fruit of the tomato plants sprinkled with Ile occurred sooner, and the numbers of blooms and fruit of the Ile-sprinkled plants were also larger, as compared to the plants receiving only water, or the Con.

ii) Ripening of Fruit

Figure 2:
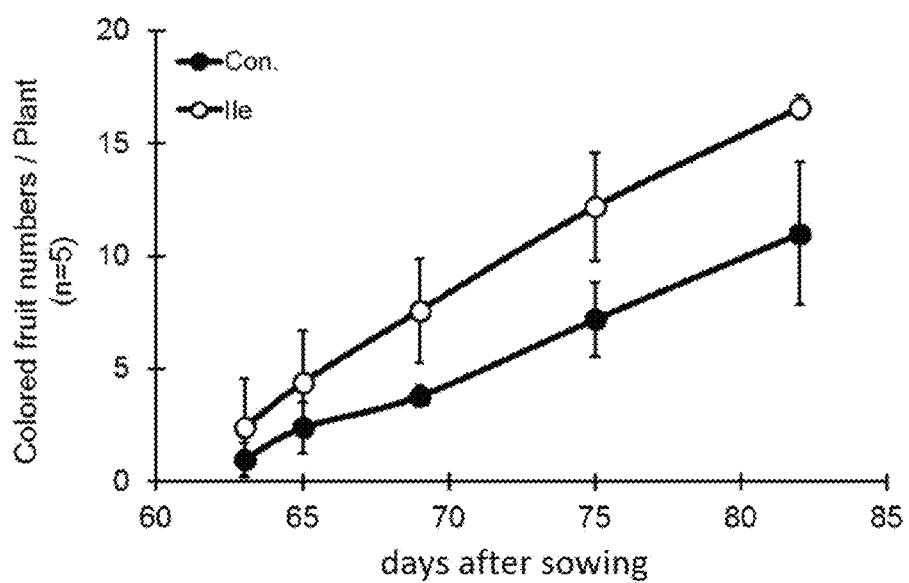
FIG. 2 shows the change of number of colored fruit of cherry tomato (Micro-Tom). The vertical axis indicates number of colored fruit per plant.

The investigation of the number of fruit that turned to the colors orange or red was performed every five days after appearance of the tomatoes, and the results are shown in FIG. 2. Ripening of the tomatoes sprinkled with Ile began earlier, and the number of tomatoes at the same time point was larger, as compared to those observed for the control (Con). It was demonstrated by these results that sprinkling of Ile has an effect of promoting the ripening or change in color of tomatoes, and the growth of the tomato plants could be promoted.

iii) Number of Fruit Produced

Figure 3:
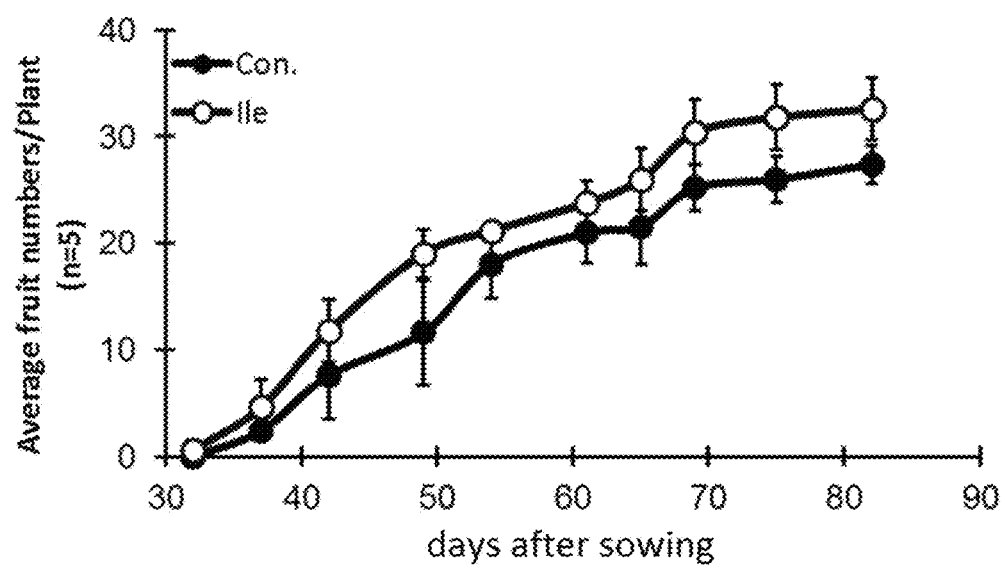
FIG. 3 shows the change of number cherry tomatoes (Micro-Tom). The vertical axis indicates average number of fruit per plant.

The results of investigation of change over time in the number of fruit produced are shown in FIG. 3. On the 82nd day after the sowing, tomatoes were harvested. The number of harvested tomatoes sprinkled with Ile was larger by 20% as compared to that of the control (Con). It is considered that this result was due to the increase of blooming number and number of fruit ratio induced by the sprinkling of Ile, and crop yield of tomato was also improved.

Example 2: Effect of Isoleucine on Tomato (Momotaro)

Three seeds of tomato (Momotaro Fight) were shown in compost contained in a slit pot, and cultivated in the same manner as described in Example 1, provided that the cultivation was performed in a greenhouse (daytime temperature was 25° C. (6:00 to 20:00), and night temperature was 15° C. (20:00 to 6:00)). The compost and application of fertilizer were the same or performed in the same manner as those described in Example 1.

After 3 weeks, one root clump was left, and the others were thinned out. When a flower cluster of the first tier appeared, a support was put up, and after a flower cluster of the second tier appeared, pinching was performed (pinching of terminal bud).

After the plants of four root clumps uniformly grew, and flower buds began to appear, water (Con.), 10 mM L-isoleucine aqueous solution (Ile), 10 mM monosodium glutamate aqueous solution (GluNa), 5 mM urea aqueous solution (Urea), or 10 mM phenylalanine aqueous solution (Phe) was sprinkled on the whole plants every two weeks. The sprinkled volume was adjusted in accordance with the growth of the plants, and it was 15 to 30 mL per one root clump. The concentration of urea was 5 mM so that nitrogen amount provided by it was the same as that provided by each of the amino acids.

Then, the first appearance of fruit, ripening of fruit, and number of fruit produced were investigated for each root clump.

i) First Appearance of Fruit

Figure 4:
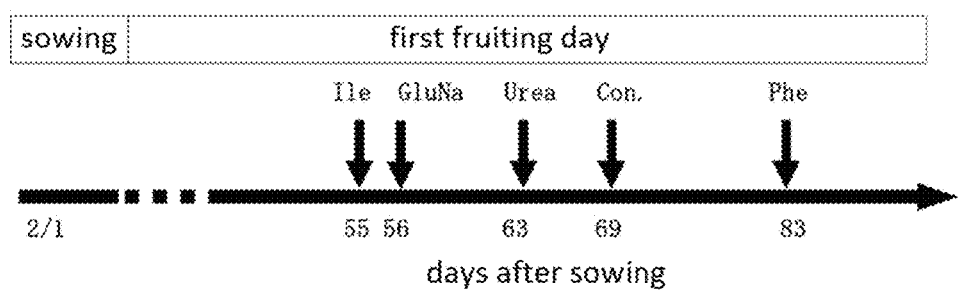
FIG. 4 is a diagram showing numbers of days required for the first appearance of fruit of tomato plants (Momotaro) sprinkled with various compounds.

The days on which each plant bore a fruit for the first time of the tomato plants sprinkled with each solution are shown in FIG. 4. Appearance of fruit was observed in the tomato plants sprinkled with Ile, GluNa, Urea, water, and Phe in the mentioned order. Whereas fruit first appeared on the tomato plant sprinkled with water on the 69th day after sowing, fruit first appeared on the tomato plant sprinkled with Ile on the 55th day after sowing. Fruit first appeared on the tomato plants sprinkled with GluNa and Urea on the 56th day and 63rd days after sowing, respectively, which was earlier than that of the tomato plant sprinkled with water (Con.). Furthermore, fruit appeared on the tomato plant sprinkled with Phe the latest, and was observed on the 83rd day after sowing. As described above, sprinkling of Ile most accelerated the appearance of fruit on the tomato plant.

ii) Coloring of Fruit

Figure 5A:
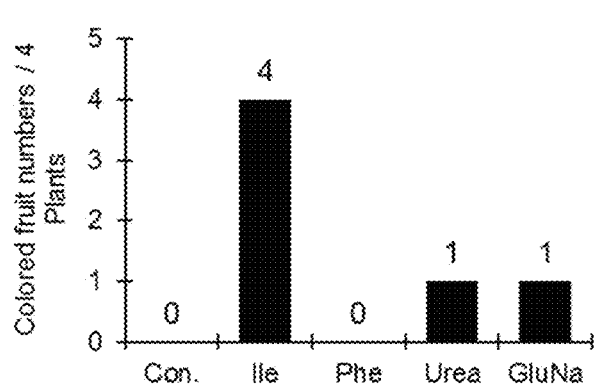
FIGS. 5a and 5b show the ripening (change in color) of tomato (Momotaro) sprinkled with various compounds.
Figure 5B:
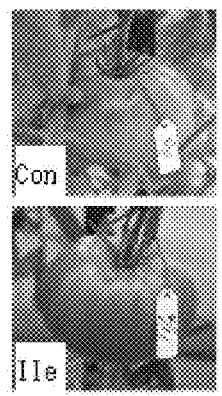

The numbers of fruit turning color to orange or red on the 107th day after the sowing of the tomato plants are shown in FIG. 5a. The numbers were 4 for the tomato plant sprinkled with Ile, 1 for the Urea and GluNa-sprinkled ones, and 0 for the water (Con.) and Phe-sprinkled ones, and thus the tomato plant sprinkled with Ile showed the largest number of tomatoes that had turned color to orange or red. Furthermore, the color of fruit obtained from flowers that bloomed on the same day were compared for the tomato plants sprinkled with water (Con.) and Ile. As a result, the fruit of the water-sprinkled tomato plant was green, but the fruit of the Ile-sprinkled tomato plant already turned color to red, i.e., turned color earlier (FIG. 5b). As described above, the fruit ripending-promoting effect of Ile was also observed for the Momotaro tomato.

iii) Number of Fruit

Figure 6:
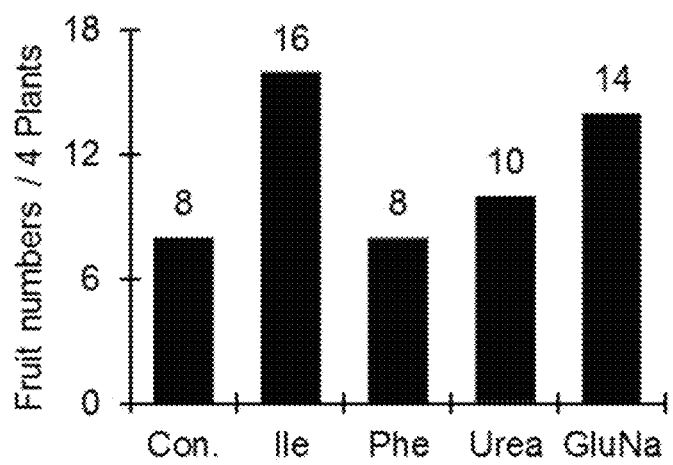
FIG. 6 shows numbers of harvested fruit of tomato plants (Momotaro) sprinkled with various compounds. The vertical axis indicates number of fruit per four root clumps.

After cultivation for 3 months after the sowing, tomato fruit were harvested. The numbers thereof are shown in FIG. 6. The numbers of the harvested fruits were 8 for the tomato plant sprinkled with water (Con.), 16 for the Ile-sprinkled one, 8 for the Phe-sprinkled one, 10 for the Urea-sprinkled one, and 14 for the GluNa-sprinkled one. As described above, the tomato appearance-increasing effect of Ile sprinkling was also observed for the Momotaro tomato, and the crop yield was also improved.

Example 3: Effect of Isoleucine on Cherry Tomato (Suncherry Pure)

Three seeds of cherry tomato (Suncherry Pure, Tokita Seed) were shown in compost contained in a slit pot, and cultivated in the same manner as described in Example 1, provided that the cultivation was performed in a greenhouse as in Example 2. The compost and application of fertilizer were the same or performed in the same manner as those described in Example 1.

One month after the sowing, each seedling was permanently planted in a 9.0-cm long pot (top diameter 9 cm, height 20 cm, bottom diameter 6.4 cm), and cultivated until harvest. As for application of fertilizer, a 200-fold diluted solution of Vegetable Life A (Otsuka Chemical) was additionally applied as a fertilizer by irrigation in a volume of 100 mL per one root clump (pot) every two days from one month after the sowing to the harvest.

After the plants of four root clumps uniformly grew, and flower buds began to appear, water (Con.), 10 mM L-isoleucine aqueous solution (Ile), or 10 mM proline aqueous solution (Pro) was sprinkled on the whole plants once a week. The sprinkled volume was adjusted in accordance with the growth of the plants, and it was 15 to 30 mL per one root clump.

Then, ripening of fruit, number of fruit, amino acid content of fruit juice, sugar content and acidity of fruit juice, and antioxidant capacity of fruit juice were investigated for each root clump.

i) Ripening of Fruit

Figure 7:
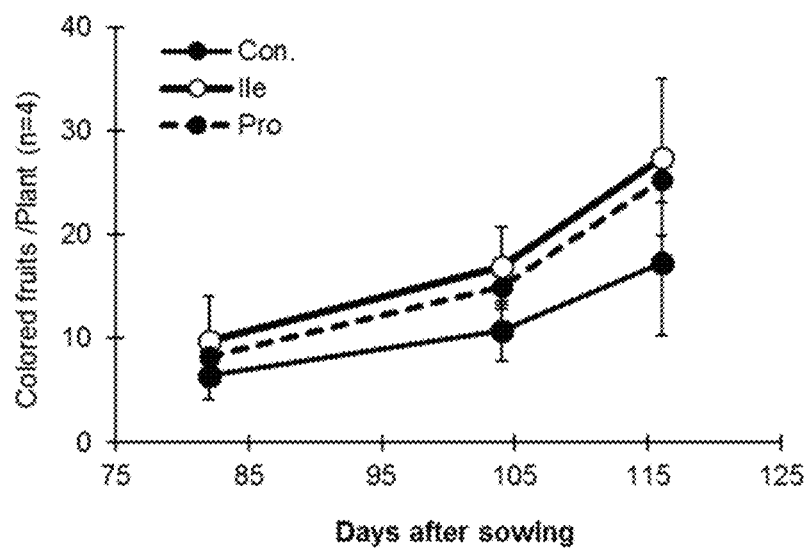
FIG. 7 shows the change of number of ripened fruit of cherry tomato plants (Suncherry Pure) sprinkled with isoleucine or proline. The vertical axis indicates number of ripened fruit per plant.

The number of fruit that had changed color are shown in FIG. 7. The number of tomatoes that had changed color were larger in the order of the tomato plants sprinkled with Ile, Pro, and water (Con.). The tomato ripening-promoting effect of sprinkling of Ile was confirmed also in this example.

ii) Number of Fruit

Figure 8:
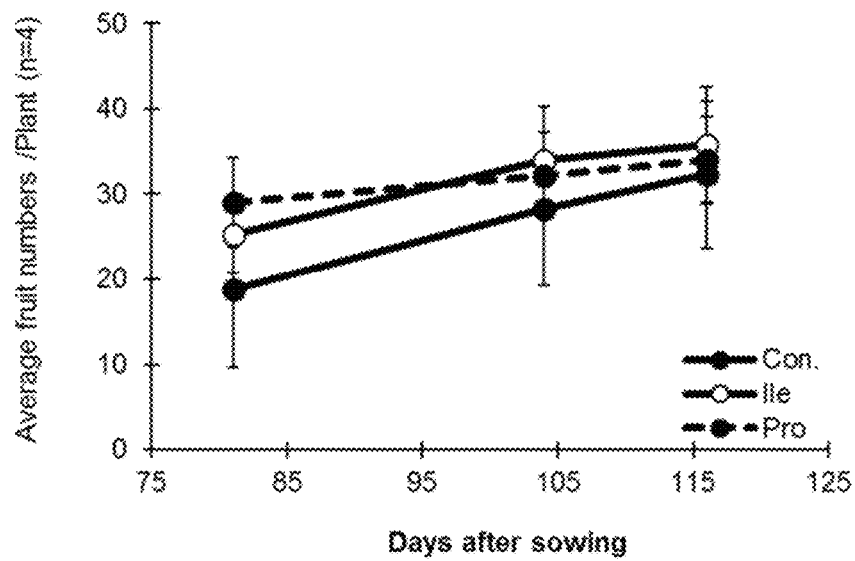
FIG. 8 shows change of number of cherry tomato plants (Suncherry Pure) sprinkled with isoleucine or proline. The vertical axis indicates number of fruit per plant.

The results of investigation of number of fruit of the tomato plants performed over time are shown in FIG. 8. In an early stage, the number of fruit produced was larger in the order of the tomato plants sprinkled with Pro, Ile, and water, but the number of fruit produced of the tomato plant sprinkled with Ile increased in the middle of the cultivation, and exceeded the number of fruit produced of the tomato plant sprinkled with Pro. As for the final crop yield, the number of fruit produced of the tomato plants sprinkled with Ile and Pro were larger by 16% and 9%, respectively, as compared to that of the tomato plant sprinkled with water (Con.).

iii) Amino Acid Analysis of Fruit

Mature fruit were taken from each of the cherry tomato plants sprinkled with water, Ile, or Pro, and the amino acid content was analyzed for each. Two pieces of fruit were taken from the flower cluster of the second tier of one root clump, that is, a total of 8 pieces of fruit were taken for each test group. Fruit juice was pressed out of each piece of fruit, and the fruit juice was diluted 10 times with 0.02 N HCl, and subjected to filter filtration. The amino acids contained in the obtained filtrate were measured. Measurement of the amino acids was performed with High Speed Amino Acid Analyzer L-8800 (Hitachi) according to the manual of this instrument. The amounts of the amino acids (μmol/mL) in each fruit juice filtrate were calculated, and the averages for eight pieces of fruit were used as the amino acid amounts of the corresponding test group.

The results are shown in Table 1. In the fruit of the tomato plants sprinkled with Ile, the amounts of glutamic acid (Glu), asparagine (Asn), glutamine (Gln), aspartic acid (Asn), proline (Pro), and methionine (Met) were reduced, but the amounts of alanine (Ala), γ-aminobutyric acid (γ-ABA), isoleucine (Ile), leucine (Leu), valine (Val), serine (Ser), glycine (Gly), threonine (Thr), lysine (Lys), histidine (His), cysteine (Cys), arginine (Arg), tyrosine (Tyr), and tryptophan (Trp) were increased as compared to the control (Con). By the sprinkling of Ile, many kinds of essential amino acids including branched chain amino acids and aromatic amino acids were increased.

Branched chain amino acids and aromatic amino acids serve as starting materials of synthesis of many plant secondary metabolites such as phenylpropanoids, flavonoids, and alkaloids. The functional amino acid, γ-ABA, was also increased. These results suggest that the secondary metabolism of the fruits was activated by the sprinkling of Ile. It can be expected that the nutrient value of the tomato is increased by the increase of the essential amino acids and the functional amino acid, γ-ABA.

TABLE 1

Amino acid analysis of tomato fruit obtained with sprinkling of Ile or Pro (μmol/mL)

|  | Total | Glu | Asp | Gln | Asn | Pro | Met | Phe | Ala |
|---|---|---|---|---|---|---|---|---|---|
| Con. | 20.56 | 7.21 | 1.62 | 1.59 | 0.61 | 0.35 | 0.13 | 0.5 | 3.42 |
| Ile | 20.25 | 6.46 | 1.33 | 1.1 | 0.55 | 0.33 | 0.09 | 0.5 | 4.51 |
| Pro | 21.13 | 7.76 | 1.75 | 1.57 | 0.63 | 0.39 | 0.14 | 0.38 | 3.79 |

TABLE 1-continued

Amino acid analysis of tomato fruit obtained with sprinkling of Ile or Pro (μmol/mL)

|      | γ-ABA | Ile  | Leu  | Val  | Ser  | Gly  | Thr  | Lys  | His  | Cys  | Arg  | Tyr   | Trp   |
|------|-------|------|------|------|------|------|------|------|------|------|------|-------|-------|
| Con. | 5.48  | 0.17 | 0.32 | 0.17 | 0.59 | 0.25 | 0.28 | 0.29 | 0.17 | 0.15 | 0.11 | 0.045 | 0.034 |
| Ile  | 6.42  | 0.23 | 0.39 | 0.21 | 0.67 | 0.35 | 0.3  | 0.33 | 0.19 | 0.21 | 0.14 | 0.082 | 0.06  |
| Pro  | 4.46  | 0.15 | 0.29 | 0.18 | 0.61 | 0.24 | 0.27 | 0.27 | 0.17 | 0.08 | 0.13 | 0.185 | 0.072 | iv) Sugar Content and Acidity Analysis

Mature tomato fruit were taken from cherry tomato plants of each experimental group in the same manner as described in iii) above, and fruit juice was pressed out from each fruit. Glucose content, fructose content, and acidity of each fruit juice extract were analyzed. Analysis of glucose and fructose was performed for a 20-fold diluted solution of fruit juice by using a food analysis reagent kit, F-Kit (Saccharose (Sucrose)/D-Glucose/D-Fructose Kit (Roche)) and DU800 Spectrophotometer (Beckman Coulter) according to the manuals of the kit and instrument. Acidity analysis was performed by using a pocket acidity meter (PAL-AC1, ATAGO).

The results are shown in Table 2. The glucose content and fructose content of the fruit of the tomato plants sprinkled with Ile were almost the same as those of the control (Con). The fruit of the tomato plants sprinkled with Pro showed the lowest glucose content and fructose content.

As for acidity, the fruit of the tomato plants sprinkled with Pro showed slightly increased acidity.

TABLE 2

Glucose content, fructose content, and acidity of tomato fruit

| Treatment | Glucose (g/L) | Fructose (g/L) | Acidity % |
|-----------|---------------|----------------|-----------|
| Con.      | 13.4          | 13.3           | 0.46      |
| Ile       | 13.3          | 13.3           | 0.46      |
| Pro       | 12.3          | 12.2           | 0.47      | v) Antioxidant Capacity

Polyphenols were extracted from the tomato fruit, and antioxidant capacities thereof were investigated.

Figure 9:
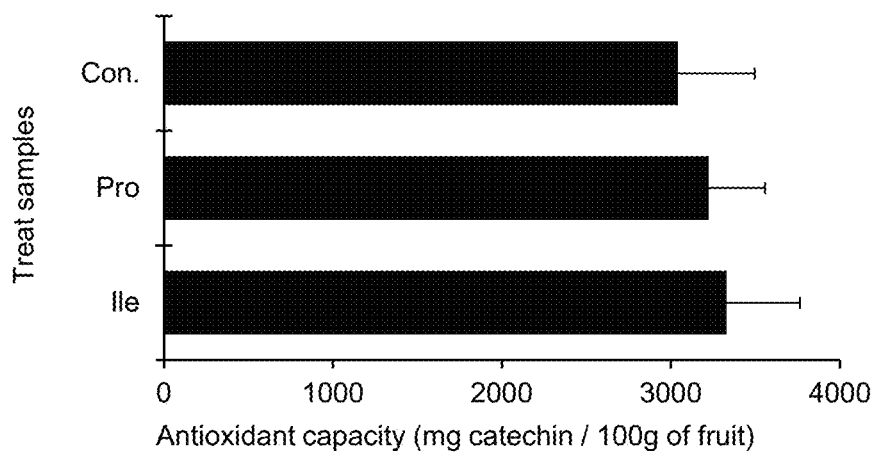
FIG. 9 shows comparison of antioxidant capacities of cherry tomato plants (Suncherry Pure) sprinkled with isoleucine or proline. The horizontal axis indicates amount of antioxidant having an ability to eliminate free radicals equivalent to that of catechin in 100 g of a sample (fresh weight).

Mature tomato fruit were taken from cherry tomato plants of each experimental group in the same manner as described in iii) as described above. The fruit were frozen in liquid nitrogen, and then ground, and 0.5 g of the powder was put into a 2-mL tube, and extracted twice with 1.0 mL of 70% methanol. Liquid of the extract was completely evaporated by using a centrifugal evaporator, and the residue was dissolved in 500 μL of 70% methanol to prepare a sample. The antioxidant capacity of the sample was measured as the free radical-eliminating ability thereof by using the DPPH (2,2-diphenyl-1-picrylhydrazyl) radical method with reference to Lamien-Meda, A. et al., Molecules, 2008, 13(3): 581-594. To 50 μL of the sample, 700 μL of methanol, and 750 μL of 0.02 mg/mL DPPH (ALFA AESAR) were added, and they were sufficiently mixed. Then, the mixture was incubated at room temperature for 15 minutes, and absorbance thereof was measured at 517 nm. A calibration curve was prepared by using 0, 0.2, 1, 2, and 4 μg/mL solutions of catechin instead of the sample. The measured free radical-eliminating ability was converted into amount (mg) of catechin having free radical-eliminating ability equivalent to that of 100 g (fresh weight) of the sample. The results are shown in FIG. 9. As a result, it was found that the tomatoes sprinkled with Ile showed higher antioxidant capacity as compared to the tomatoes sprinkled with water (Con.) or Pro.

vi) Others

Figure 10:
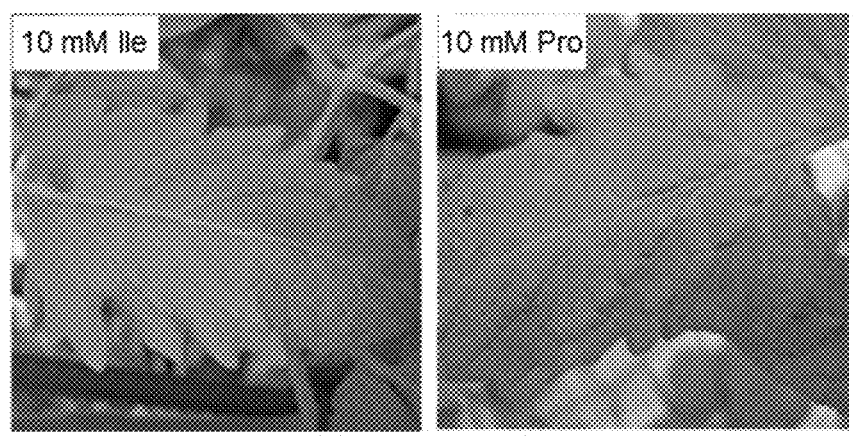
FIG. 10 includes photographs showing sunscald of cherry tomato plants (Suncherry Pure) sprinkled with proline (morphologies of plants).

Whereas black spots of sunscald were observed on the leaves of the tomato plants sprinkled with Pro, sunscald was not seen in the tomato plants sprinkled with Ile (FIG. 10).

From the results as described above, it was found that sprinkling of Ile can improve crop yield and quality of tomato in a short period of time.

Example 4: Effect of Isoleucine on Coloring and Carotenoid Synthesis of Tomato

A 10 mM isoleucine (Ile) aqueous solution was sprinkled on immature pieces of fruit all having the substantially same size, taken from flower clusters of the same tier of tomato plants cultivated in the same manner as described in Example 3, and the ripening of the fruit was investigated.

The fruit were put into two 100-mL glass beakers in a number of six each. 1 mL of water (Con.) was sprinkled on the fruit in one beaker, and 1 mL of an Ile solution was sprinkled on the fruit in the other beaker. Then, the beakers were closed with plastic wrap, and left for 5 hours; then the wrap was removed, and the fruit were left as they were. The test was performed at room temperature, and the sprinkling of water and Ile solution was performed twice in total at an interval of one week.

The color and appearance of three pieces of fruit out of the six for each group was recorded at the time of the start of the test, and 27, 32, and 34 days after the start of the test. Around the 27th day, the fruit sprinkled with Ile began to turn color, whereas the fruit of the control sprinkled with water (Con) were still green. Around the 34th day, the fruit sprinkled with Ile turned color to a fully mature red, whereas the fruit sprinkled with water were still a half-mature orange color. The results are shown in FIG. 11a.

Figures 11A, 11B:
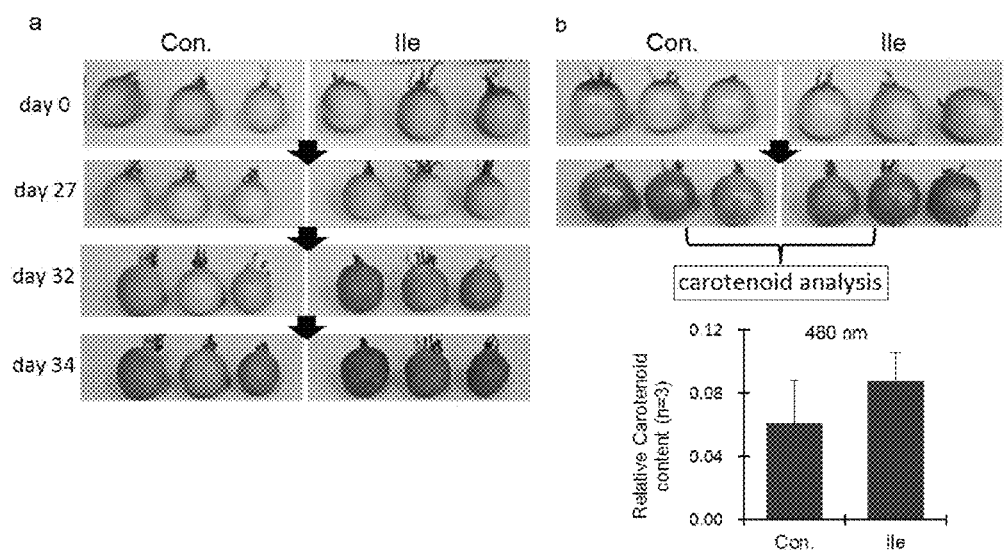
FIGS. 11a and 11b includes photographs (appearance of fruits) showing ripening of tomatoes (Suncherry Pure) sprinkled with isoleucine, and a graph showing results of carotenoid analysis thereof. The vertical axis of the graph indicates relative content of carotenoid.

Furthermore, the carotenoid content of the three remaining fruit were measured by the following methods around the 27th day after the start of the test (FIG. 11b). The tomato fruit of which seeds were removed were frozen with liquid nitrogen, and ground in a mortar. The ground sample (0.5 mg) was put into a 2-mL tube, 1 mL of chloroform was added, and extraction was performed in a shaker (Micro & Shaker, IUCHI) for 10 minutes with vibration. The extraction mixture was centrifuged for 5 minutes (8000 rpm), and the chloroform layer as the lower layer was transferred to a new tube. Chloroform (0.5 mL) was added again to the former tube, extraction was performed in the same manner, and the chloroform layer was fully taken out, and transferred to the latter tube containing the aforementioned chloroform extract. Then, chloroform was evaporated from the obtained extract by using a centrifugal evaporator. Then, a sample solution was prepared by adding 0.5 mL of chloroform to the residue to dissolve it, and carotenoids contained in the sample solution were analyzed. For the measurement of carotenoids, the extraction sample was diluted 100 times with chloroform, and absorbance thereof was measured at the extinction wavelength of carotenoids (480 nm) by using DU800 Spectrophotometer (Beckman Coulter). The results are shown in FIG. 11b.

As shown in FIG. 11, it was found that the carotenoid content of the tomato fruit sprinkled with Ile was higher than that of the fruit treated with water on the basis of visible evaluation (FIG. 11a) and evaluation based on carotenoid quantification (FIG. 11b). These results revealed that the carotenoid synthesis and ripening of fruit were promoted by sprinkling of Ile on the fruit.

Example 5: Relation of Sprinkling of Isoleucine and Jasmonic Acid

A 10 mM isoleucine aqueous solution (Ile) or water (Con.) was sprinkled on leaves of cherry tomato plants (Suncherry Pure) cultivated in the same manner as described in Example 3, and expression of genes relevant to jasmonic acid were analyzed. Three hours after the foliar application, leaves of the same part were collected, and RNA was isolated by using SV Total RNA Isolation System™ (Promega) according to the manual of the kit. By using RiverTraAce™ qPCR RT Master Mix (TOYOBO), primary cDNA chains were synthesized from the extracted RNA.

i) Analysis of Genes Involved in Jasmonic Acid Synthesis

Figure 12:
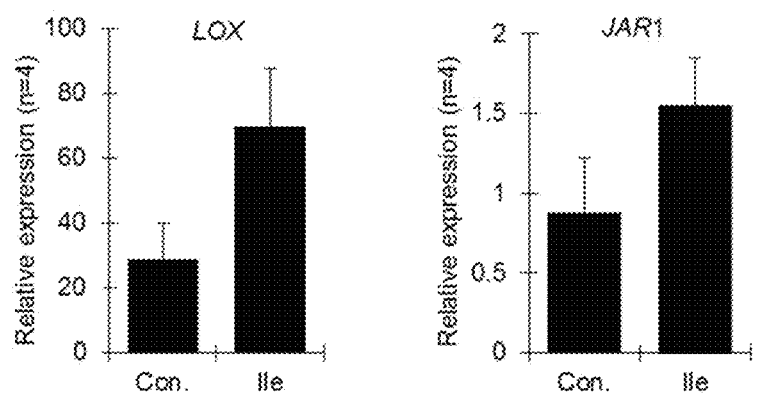
FIG. 12 includes graphs showing expressions of the LOX and JAR1 genes involved in the jasmonic acid synthesis observed in cherry tomatoes (Suncherry Pure) sprinkled with isoleucine. The vertical axes indicate the relative expression amount.

Expression of the 13-lipoxygenase (LOX) gene locating in the upstream of the jasmonic acid biosynthesis pathway, and the gene for synthesis of JA-Ile from JA and Ile (JASMONATE RESISTANT 1 (JAR1)) were analyzed. Real-time PCR was performed by using the aforementioned cDNAs as the template, and the primers shown in Table 3. The expression amounts of the genes are represented as relative expression amounts with respect to that of the actin gene. The results are shown in FIG. 12.

Expression of the LOX gene and JAR1 gene in the leaves of the tomato plant sprinkled with Ile were significantly higher than those in the same of the tomato plant sprinkled with water (Con.).

TABLE 3

Primers for real-time PCR

| Primer name | Sequence (5'-3') | SEQ ID NO: |
|---|---|---|
| Primers for tomato | | |
| Actin-F | CACCATTGGGTGTGAGCGAT | 1 |
| Actin-R | GGGCGACAACCTTGATCTTC | 2 |
| JAR1-F | GTGTTGACTAAAGATGCTGGG | 3 |
| JAR1-R | GGTGAAAGATCACCATCAGCAA | 4 |
| LOX-F | CGGTTTTGTCCATGGCAAAG | 5 |
| LOX-R | ACCGTCAGGATCACCGATATC | 6 |
| PI-F | GTTGATGCCAAGGCTTGTACT | 7 |
| PI-R | CAACATGTGGTACATCCGGT | 8 |

TABLE 3-continued

Primers for real-time PCR

| Primer name | Sequence (5'-3') | SEQ ID NO: |
|---|---|---|
| MYC2-F | AGGGTCGTCTAGTTCAGCAG | 9 |
| MYC2-R | TGGGCTTGAACTGTACATCGCCAA | 10 |
| Psy-F | TTGGGCTTGTTGAGTGAAGC | 11 |
| Psy-R | TGTCGTTGCCTTGATTCAGG | 12 |
| Pds-F | TTGTGTTTGCCGCTCCAGTGGAT | 13 |
| Pds-R | GCGCCTTCGATTGAAGCCAAGTA | 14 |
| Zds-F | ATTATTACATTGAGGGACAAGGC | 15 |
| Zds-R | TCATCAGACAAGACTCAACTGAT | 16 |
| Primers for pepper | | |
| LOX-F | AGACAAGCACTCCCTGAGGACC | 17 |
| LOX-R | AACTCTGGCCACCATGGCTCA | 18 |
| Psy-F | TGCTTTCGCTGCAGTGCCAGA | 19 |
| Psy-R | TGTCTAGCGCACAACCGTCAAGG | 20 | ii) Analysis of Genes that Respond to Jasmonic Acid

Figure 13:
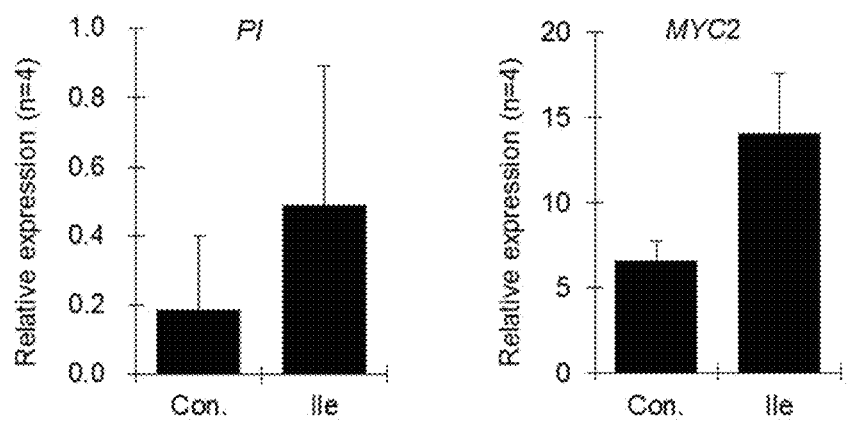
FIG. 13 includes graphs showing expression of the jasmonic acid response genes PI and MYC2 observed in cherry tomatoes (Suncherry Pure) sprinkled with isoleucine. The vertical axes indicate the relative expression amount.

The results of real-time PCR analysis of the jasmonic acid responding genes, protease inhibitor (PI) and MYC2 genes, performed by using the aforementioned cDNAs as the template are shown in FIG. 13. The chosen primers are shown in Table 3. By the sprinkling of Ile, expression of the PI and MYC2 genes were increased.

iii) Analysis of Genes Involved in Carotenoid Synthesis

A 10 mM isoleucine aqueous solution (Ile) or water (Con.) was sprinkled on leaf surfaces of cherry tomato plants, and RNA was isolated from the leaves 24 hours afterward. By using the isolated RNA, expression of the genes that participate in the biosynthesis of carotenoids, genes of phytoene synthase (Psy), phytoene desaturase (Pds), and ξ-carotene desaturase (Zds), were analyzed. The extraction of RNA, synthesis of cDNA, and real-time PCR analysis were conducted in the same manner as described above. The chosen primers are shown in Table 3.

Figure 14:
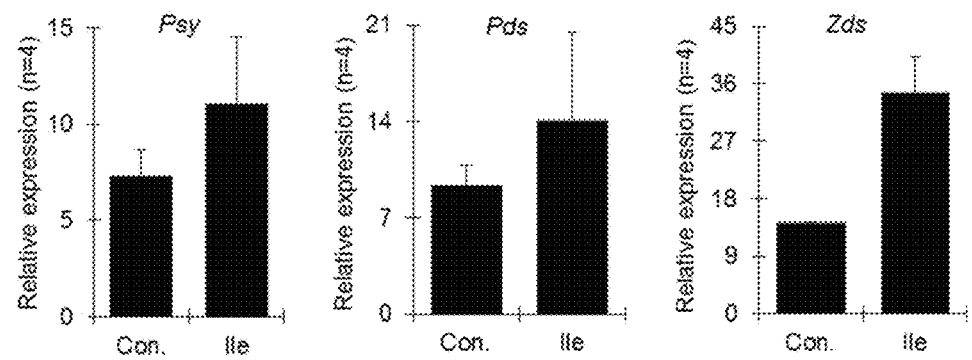
FIG. 14 shows expression of genes involved in the carotenoid biosynthesis observed in cherry tomatoes (Suncherry Pure) sprinkled with isoleucine. The vertical axes indicate the relative expression amount.

The results are shown in FIG. 14. In the tomato plant sprinkled with Ile, expression of Psy, Pds, and Zds were increased.

Example 6: Investigation of Isoleucine Concentration for Sprinkling (I)

Cherry tomato plants were cultivated in the same manner as described in Example 3, and 20 mL of a 1 mM, 4 mM, 7 mM, or 10 mM isoleucine aqueous solution (Ile) was sprinkled on leaf surfaces and fruits of each plant. One week afterward, Ile was sprinkled again in the same manner, the leaves were collected 3 hours thereafter, and expression of the LOX, JAR1, PI and MYC2 genes were analyzed in the same manner as described in Example 5. The chosen primers are shown in Table 3.

Figure 15:
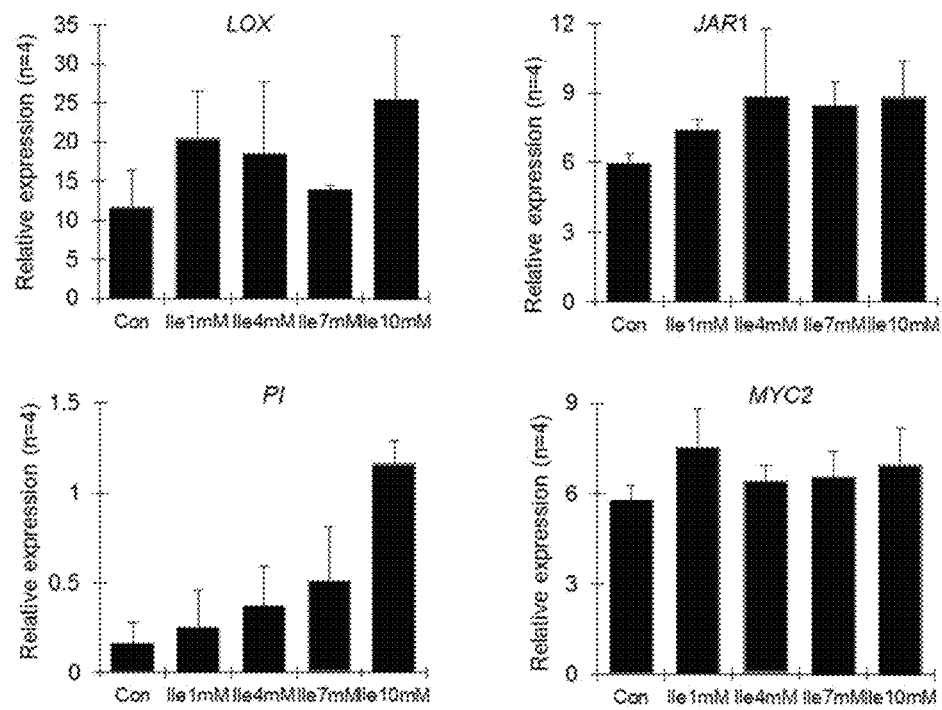
FIG. 15 includes graphs showing expression of the LOX, JAR1, PI, and MYC2 genes observed in cherry tomatoes (Suncherry Pure) sprinkled with isoleucine at various concentrations. The vertical axes indicate the relative expression amount.

The results are shown in FIG. 15. Expression of the genes increased substantially in an Ile concentration-dependent manner.

Example 7: Investigation on Isoleucine Concentration for Sprinkling (II)

Figure 16:
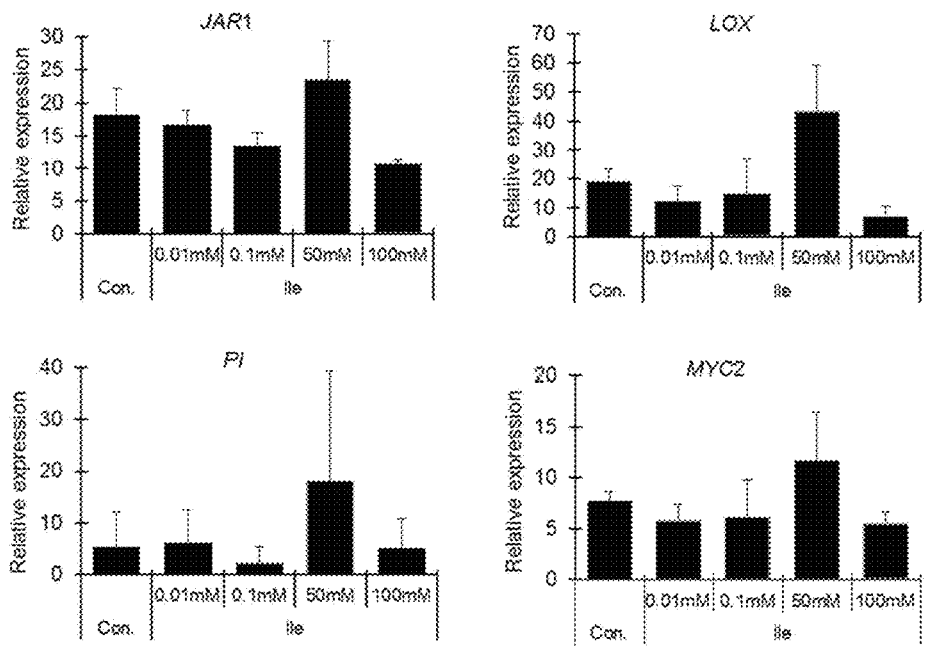
FIG. 16 includes graphs showing expressions of the LOX, JAR1, PI, and MYC2 genes observed in cherry tomatoes (Caddy) sprinkled with isoleucine at various concentrations. The vertical axes indicate the relative expression amount.

Tomato plants (variety: Caddy, Tokita Seed) were cultivated in a biotron room in the same manner as described in Example 1. Three weeks after sowing, 3 mL of water, or a 0.01 mM, 0.1 mM, 50 mM, or 100 mM isoleucine aqueous solution (Ile) was sprinkled on leaf surfaces of each plant, sampling was performed from the second foliage leaves, and expression of LOX, JAR1, PI and MYC2 genes were analyzed in the same manner as described in Example The results are shown in FIG. 16. Expression of the genes was promoted by sprinkling of 50 mM of Ile.

On the basis of this result together with the results of Example 6, it is considered that the Ile concentration can be not lower than 0.5 mM and not higher than 75 mM.

Example 8: Effect of Isoleucine on Pepper

A 10 mM isoleucine aqueous solution (Ile) was sprinkled on pepper plants (variety, Anaheim), which also belong to the family Solanaceae, like tomato, and gene expression analysis was performed. The pepper plants were cultivated in a greenhouse in the same manner as described in Example 2.

Ile was sprinkled once a week, and after the second sprinkling, leaves were collected from the pepper plants. RNA extraction, cDNA synthesis, and real-time PCR were performed in the same manner as described in Example 5 to analyze gene expression. Expression of the LOX gene was analyzed by using leaves collected 3 hours after the second sprinkling, and expression of the Psy gene was analyzed by using leaves collected 24 hours after the second sprinkling. The chosen primers are shown in Table 3.

Figure 17:
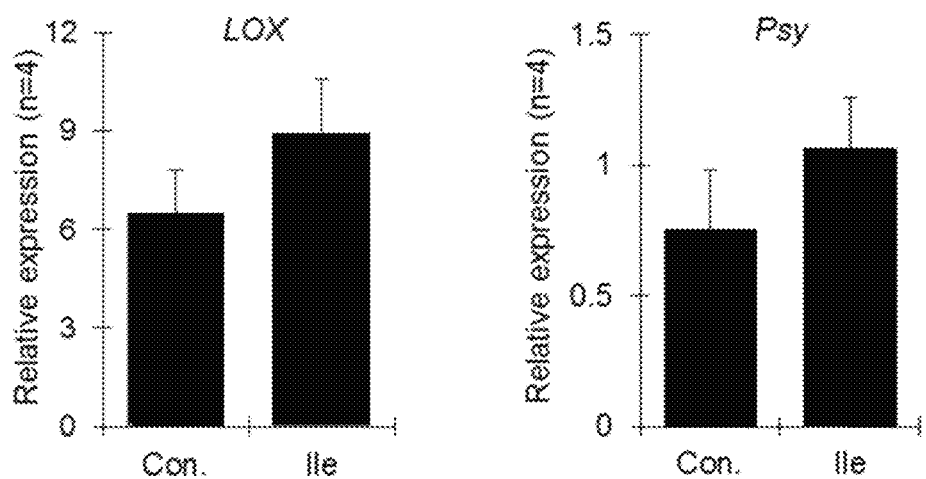
FIG. 17 includes graphs showing expression of the LOX, and Psy genes observed in pepper (Anaheim) sprinkled with isoleucine. The vertical axes indicate the relative expression amount.

The results are shown in FIG. 17. Expression of the LOX and Psy genes of the pepper plants sprinkled with Ile were higher than those observed for Con.

Since the jasmonic acid pathway and the carotenoid pathway were activated by sprinkling of Ile also in pepper plants, which belong to the family Solanaceae like tomato, similar effects of sprinkling of Ile can be generally expected for the Solanaceae plants.

Example 9: Ripening-Promoting Effect and Harvestable Bunch Number-Increasing Effect of Isoleucine on Middle Size Fruit-Bearing Tomato For the test, middle size fruit-bearing tomato plants in the second half of their growth (variety, Tsukutsuku-shi) that were cultivated in a greenhouse and bore fruit of the 12th tier were used. Neighboring 12 root clumps of the tomato plants were selected, 6 root clumps of them were used for control group receiving no treatment, and the other 6 root clumps were used for the Ile treatment group. As fruit used for the test, 10 bunches each of substantially uncolored fruit were chosen from those of the 9th and 10th tiers of the plants of the no treatment group and isoleucine (Ile) treatment group, and labeled. For the Ile treatment group, an Ile aqueous solution containing 3 mM Ile and a spreading agent (0.2% Squash, MARUWA Biochemical) was sprinkled on the objective fruit and leaves of the whole plant, and the plants of the no treatment group were not sprinkled with any substance. The total volume of the solution sprinkled on the plants of 6 root clumps was 600 ml. After the treatment, the change in color of tomatoes was confirmed and harvested from each bunch on 11th, 8th, and 27th days.

Figure 18:
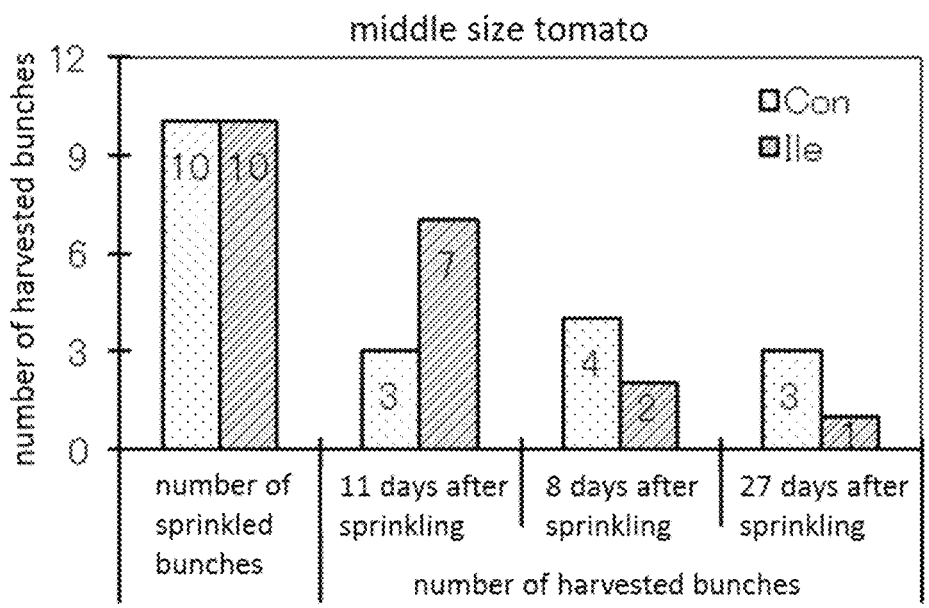
FIG. 18 shows number of harvested bunches of ripened middle size tomatoes (Tsukutsuku-shi) sprinkled with isoleucine.

When substantially all the fruit colored (ripened), or many fruit were ready to overmature, that is, when the top of the fruit was still green, the fruit were harvested. The numbers of bunches harvested on the 11th day after the treatment were 3 for the no treatment group, and 7 for the Ile treatment group. The numbers of bunches harvested on the 18th day after the treatment were 4 for the no treatment group, and 3 for the Ile treatment group. The numbers of bunches harvested on the 27th day after the treatment were 3 for the no treatment group, and 1 for the Ile treatment group (FIG. 18). As seen from these results, the change in color of the tomatoes was accelerated in the Ile treatment group, and it was suggested that Ile promoted the change in color of the tomatoes. Among the harvested fruit of 10 bunches, the total 85 fruit of the no treatment group included 15 unripened (green) fruit, but the total 86 fruit of the Ile treatment group included only 8 immature fruits, which means that sprinkling of Ile decreased the number of unripened fruits.

Example 10: Effect of Isoleucine Fermentation by-Produced Liquid on Pepper (Bell Pepper)

Figure 19:
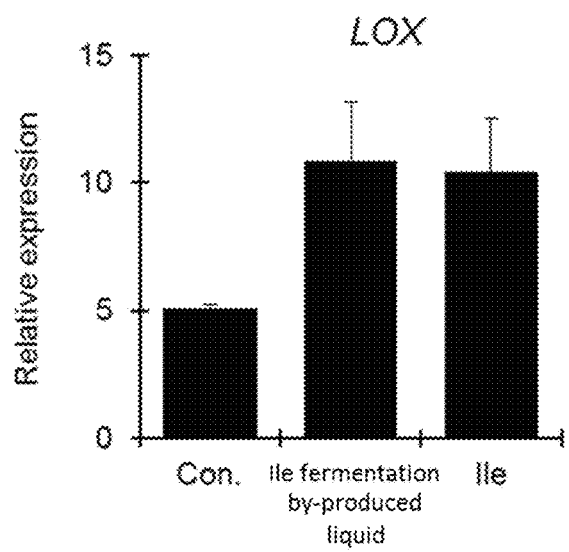
FIG. 19 shows expression of the LOX gene observed in pepper (bell pepper, Frupyred EX) sprinkled with isoleucine fermentation by-produced liquid. The vertical axis indicates the relative expression amount.

Expression of the LOX gene involved in the jasmonic acid pathway was investigated in a pepper plant (bell pepper, variety: Frupyred EX) sprinkled with an isoleucine (Ile) fermentation by-produced liquid. A diluted solution of Ile fermentation by-produced liquid (Ile concentration, 2.34% (W/V)) was sprinkled on leaves of the bell pepper plant, and expression of the LOX gene was investigated in the same manner as described in Example 5. The concentration of sprinked Ile fermentation by-produced liquid was 3.8 mM. The results are shown in FIG. 19. Induction of the LOX gene expression similar to that observed with a similar concentration of Ile was also observed with the Ile fermentation by-produced liquid.

Example 11: Effect of Isoleucine on Grape (1) Effects of isoleucine and various amino acids on coloring of grape cultured cells A cell line (VR, management number RPC00003) derived from European grape (*Vitis vinifera* L.) and stored in the Institute of Physical and Chemical Research, BioResource Center was subcultured on the MS agar medium. The subcultured VR callus was transferred to the MS agar medium containing a 5 mM solution of a different amino acid, and cultured. For the positive control, abscisic acid (ABA), for which coloring-promoting effect is known, was used at 100 µM (Jeong et al., Plant Science, 167:247-252, 2004). On the 5th day after the transfer, the callus was lyophilized and ground, and anthocyanin was extracted from it by using a 1% HCl/MeOH solution. Absorbance of the extract was measured at 530 nm, and the content of anthocyanin was measured by using cyanidine 3-glucoside as a standard substance. A relative content of anthocyanin that had accumulated in the callus of each amino acid treatment group was determined with respect to the anthocyanin content of the callus of the positive control, which was taken as 100%.

The results are shown in Table 4. The callus treated with isoleucine (Ile) showed the highest anthocyanin content.

TABLE 4

Anthocyanin content analysis of grape calluses treated with amino acids

| | Amino acid | | | | | | | | | |
|---|---|---|---|---|---|---|---|---|---|---|
| | Pro | Ile | Asp | Glu | Ser | Asn | Gln | Gly | His | Arg |
| Relative anthocyanin content | 27% | 76% | 11% | 4% | 38% | 38% | 18% | 23% | 29% | 9% |

| | Amino acid | | | | | | | | | |
|---|---|---|---|---|---|---|---|---|---|---|
| | Val | Met | Ala | Trp | Phe | Cys | Leu | Thr | Lys | Try |
| Relative anthocyanin content | 6% | 42% | 7% | 4% | 40% | 6% | 30% | 35% | 15% | 0% |

Figure 20:
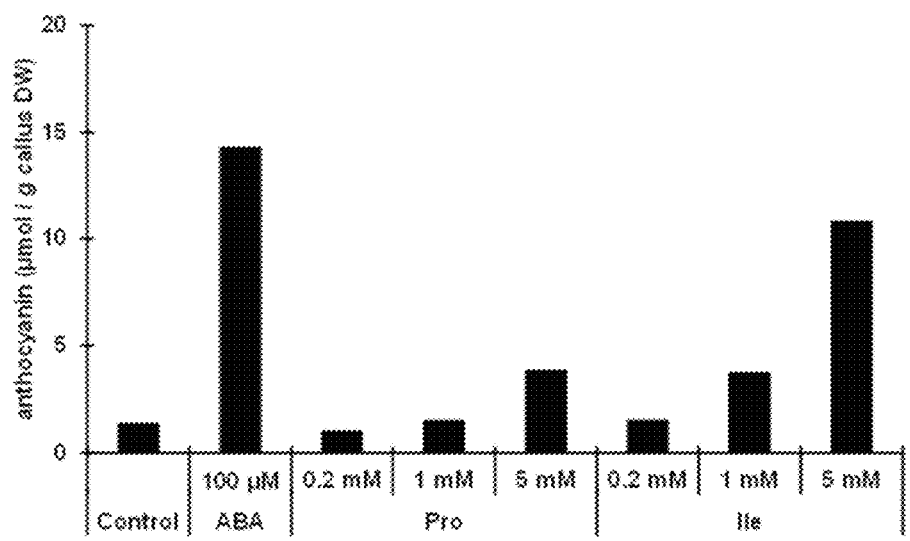
FIG. 20 shows the anthocyanin content of grape calluses treated with isoleucine. The vertical axis indicates the amount of anthocyanin (μmol/g dry weight of callus).

(2) In the same manner as described above, anthocyanin content of grape calluses treated with isoleucine and proline, respectively, were measured. The results are shown in FIG. 20. a change in color of the grape callus was promoted by a treatment with isoleucine (Ile) of 1 mM or higher. Although a change in color was also observed for the proline (Pro) treatment group, the effect was weaker than that of the Ile treatment.

(3) Effect of isoleucine on coloring of grape

Figure 21:
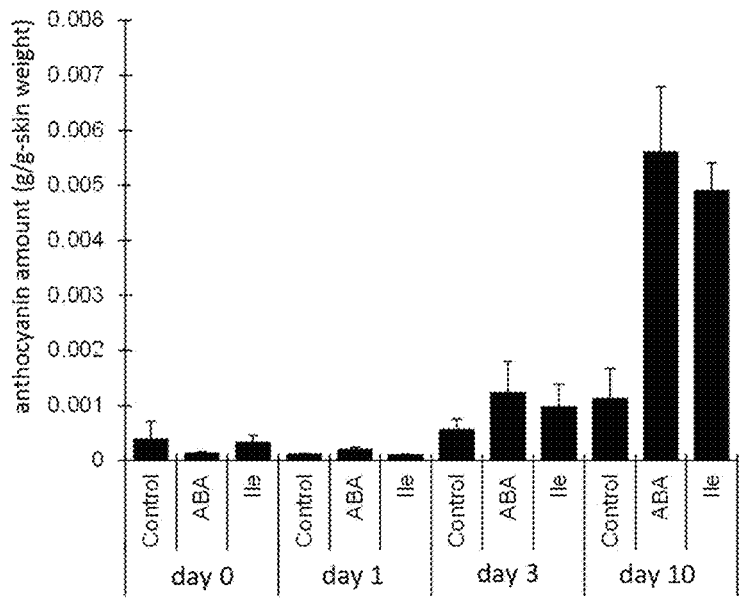
FIG. 21 shows the anthocyanin content of grapes sprinkled with isoleucine.

For the test, Cabernet Sauvignon plants that had been cultivated in a test cultivation field and had begun veraison were used. Eight bunches of fruit of the grape were collected from each of two root clumps, i.e., total 16 bunches of fruit were collected, and 6.25 mL per bunch of 0.1% Applauch BI (Kao, control), 1 g/L of abscisic acid (ABA)+0.1% Applauch BI (positive control), or 10 mM isoleucine+0.1% Applauch BI were sprinkled on them. The samples were collected 4 times, and they were collected from 4 bunches for each time. Anthocyanin contained in pericarp was extracted with a mixed solution of water and acetone (1:2) from pericarp, and anthocyanin content was measured in the same manner as described above. The results are shown in FIG. 21. It was demonstrated that treatment of the grapes with Ile increases anthocyanin content of pericarp.

Example 13: Effect of Isoleucine on Coloring of Apple

Apples (variety, Tsugaru) ready to mature (before coloring) were harvested, washed with tap water and then with distilled water, and immersed into water (control) and isoleucine (Ile) aqueous solutions of various concentrations for 15 minutes. To each treatment solution, 0.1% Applauch BI (Kao) was added. The treatment groups consisted of the following groups.
  i) Control (water)
  ii) 1 mM Ile
  iii) 5 mM Ile
  iv) 10 mM Ile
  v) 0.4 mM Methyl jasmonate (MeJA)
  vi) 10 mM Ile+1 mM Amisoft™ (anionic surfactant, sodium cocoyl glutamate)

After the treatment, the apples were air-dried, and left standing in an incubator. The conditions consisted of constant temperature of 20° C., lighting condition of 120 µM/m$^2$/s obtained with 9 of 40 W fluorescent lamps, and daylength conditions of 16 hours of light period and 8 hours of dark period per day.

Pericarp color of the apples was evaluated by measuring anthocyanin content. Pericarp (0.5 g) collected from an apple of each treatment group was immersed in 5 mL of 2% formic acid at 4° C. for 24 hours to extract anthocyanin. Anthocyanin contained in the extract was analyzed by liquid chromatography. Since most part of anthocyanin of apple consists of cyanidin galactosides, anthocyanin concentration was calculated as cyanidin galactoside concentration.

Figure 22:
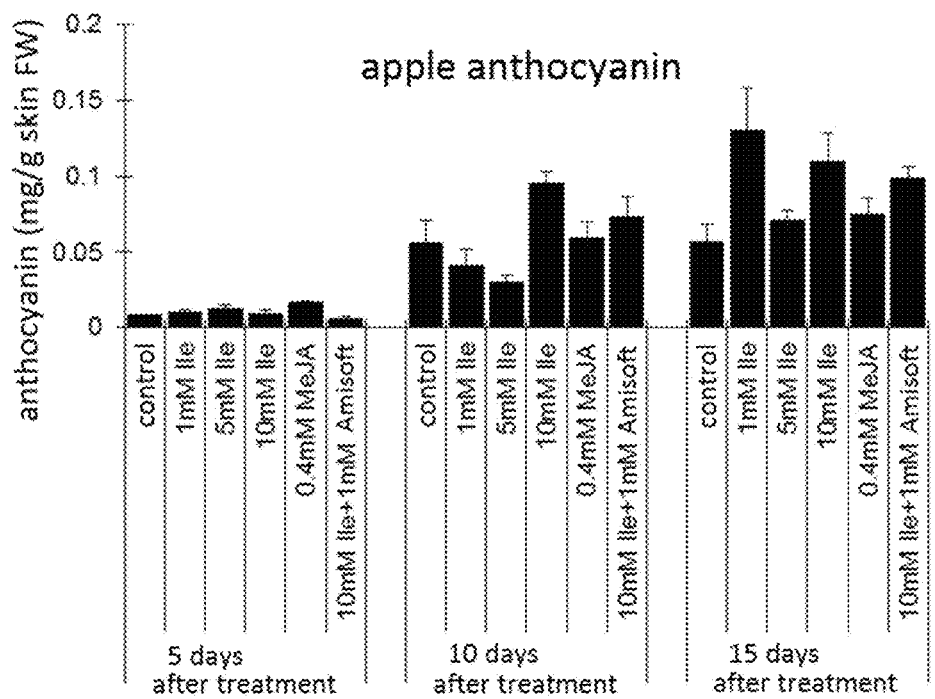
FIG. 22 shows the anthocyanin content of apples sprinkled with isoleucine.

The results are shown in FIG. 22. It can be seen that when the apples were treated with Ile, higher anthocyanin contents were observed on the 10th and 15th days after the treatment as compared to the control group.

INDUSTRIAL APPLICABILITY

The composition for agricultural or horticultural application of the present invention has action or actions for at least one of promotion of blooming, promotion of the appearance of fruits, promotion of ripening of fruits, improvement in number of fruit produced, improvement in essential amino acid and/or γ-ABA content, promotion of expressions of genes involved in jasmonic acid synthesis, and promotion of expression of genes involved in carotenoid synthesis of plants such as tomato and pepper plants. It is expected that plants can be matured in a shorter period of time by promotion of expression of genes involved in jasmonic acid synthesis.

The composition for agricultural or horticultural application of the present invention can promote the ripening of harvested fruits.

On the basis of the effects as described above, the composition for agricultural or horticultural application of the present invention can improve crop yield and/or quality of plants in a short period of time.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for cultivating a plant, which comprises sprinkling a solution consisting of 0.5 to 75 mM of isoleucine on a leaf surface and/or a fruit of a fruit vegetable, a fruit tree, or a grain plant,
wherein the sprinkling of the solution provides an effect selected from the group consisting of:
a) promotion of blooming,
b) promotion of the appearance of fruit,
c) improvement in the number of fruit produced,
d) promotion of changing in color of fruit,
e) promotion of carotenoid synthesis or anthocyanin synthesis, and
f) combinations thereof.

2. The method according to claim 1, wherein said solution consisting of 0.5 to 75 mM of isoleucine is selected from the group consisting a solution of purified isoleucine, a solution of a fermentation liquid or a fermentation by-product of isoleucine, and a solution of a fractionation product of a fermentation liquid or fermentation by-product of isoleucine.

3. The method according to claim 1, wherein the solution is sprinkled on a fruit vegetable or a fruit tree.

4. The method according to claim 3, wherein the plant belongs to the family Solanaceae, Vitaceae, or Rosaceae.

5. The method according to claim 4, wherein the plant is able to produce a fruit selected from the group consisting of tomato, pepper, grape, and apple.

6. A method for promoting ripening after harvest of a fruit, which comprises sprinkling a solution consisting of 0.5 to 75 mM of isoleucine on a harvested fruit,
wherein the sprinkling of the solution provides an effect selected from the group consisting of:
a) promotion of changing in color of the fruit, and
b) promotion of carotenoid synthesis or anthocyanin synthesis of the fruit.

7. The method according to claim 6, wherein isoleucine is L-isoleucine.

8. The method according to claim 6, wherein solution consisting of 0.5 to 75 mM of isoleucine is selected from the group consisting of a solution of purified isoleucine, a solution of a fermentation liquid or a fermentation by-product of isoleucine, and a solution of a fractionation product of a fermentation liquid or a fermentation by-product of isoleucine.

9. The method according claim 6, wherein the fruit is a fruit of a plant belonging to the family Solanaceae, Vitaceae, or Rosaceae.

10. The method according to claim 9, wherein the fruit is tomato, grape, or apple.

* * * * *

SEQUENCE LISTING

<160> NUMBER OF SEQ ID NOS: 20

<210> SEQ ID NO 1
<211> LENGTH: 20
<212> TYPE: DNA

```
<213> ORGANISM: Artificial Sequence
<220> FEATURE:
<223> OTHER INFORMATION: primer

<400> SEQUENCE: 1
caccattggg tgtgagcgat                                                 20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gggcgacaac cttgatcttc                                                 20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gtgttgacta aagatgctgg g                                               21

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ggtgaaagat caccatcagc aa                                              22

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cggttttgtc catggcaaag                                                 20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
accgtcagga tcaccgatat c                                               21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gttgatgcca aggcttgtac t                                               21
```

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
caacatgtgg tacatccggt                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agggtcgtct agttcagcag                                               20

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tgggcttgaa ctgtacatcg ccaa                                          24

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ttgggcttgt tgagtgaagc                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgtcgttgcc ttgattcagg                                               20

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
ttgtgtttgc cgctccagtg gat                                           23

<210> SEQ ID NO 14
<211> LENGTH: 23
<212> TYPE: DNA
<213> ORGANISM: Artificial Sequence
<220> FEATURE:

<223> OTHER INFORMATION: primer

<400> SEQUENCE: 14
gcgccttcga ttgaagccaa gta                                                  23

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
attattacat tgagggacaa ggc                                                  23

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
tcatcagaca agactcaact gat                                                  23

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
agacaagcac tccctgagga cc                                                   22

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
aactctggcc accatggctc a                                                    21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
tgctttcgct gcagtgccag a                                                    21

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
tgtctagcgc acaaccgtca agg                                                  23